United States Patent [19]

Bingham

[11] 4,177,195

[45] Dec. 4, 1979

[54] ORGANIC PIGMENTS DERIVED FROM BENZOCOUMARIN

[75] Inventor: Richard C. Bingham, Wilmington, Del.

[73] Assignee: E. I. Du Pont de Nemours and Company, Wilmington, Del.

[21] Appl. No.: 898,443

[22] Filed: Apr. 20, 1978

[51] Int. Cl.² .................. C07D 311/92; C07D 405/14
[52] U.S. Cl. ............................ 260/343.21; 260/326 D; 548/305
[58] Field of Search ...................... 260/343.21, 326 D; 548/305

[56] References Cited

U.S. PATENT DOCUMENTS 3,509,177  4/1970  McIntyre ........................ 260/343.45

FOREIGN PATENT DOCUMENTS 1470053  2/1967  France .

OTHER PUBLICATIONS

Bassignana et al., Tetrahedron, vol. 20, 1964, pp. 2859–2871, AD. 241T4.
Chemical Abstracts, 9th Collective, 24398cs.
Chemical Abstracts, 7th Collective, 14856s.

*Primary Examiner*—Natalie Trousof
*Assistant Examiner*—Jane T. Fan

[57] ABSTRACT

This application teaches that yellow to orange organic pigments may be produced by reacting a benzocoumarin with a selected aromatic diamine.

9 Claims, No Drawings

ORGANIC PIGMENTS DERIVED FROM BENZOCOUMARIN

BACKGROUND OF THE INVENTION

This invention relates to benzocoumarin derivatives which are useful as pigments that are primrose yellow to orange in color.

Heavy metal yellow pigments such as lead chromate, cadmium sulfide, and nickel titanate have been widely used in the paint and plastics industry for many years. However, the potential toxicity and environmental problems associated with their production and use has recently caused industry to search for alternatives to these heavy metal pigments.

Organic yellow pigments free from heavy metals provide a possible alternative to the inorganic yellows currently in use. Such alternatives must, however, offer excellent bleedfastness and durability. They also must offer bright intense shades so that they may be extended with a white pigment, such as $TiO_2$, to obtain needed opacity while retaining the needed color strength. The available organic yellow pigments do not satisfy all of these requirements.

There are six basic types of organic yellow pigments currently in use (Reference: J. Lenoir in "The Chemistry of Synthetic Dyes", Vol. V, K. Venkataramen, Ed., Academic Press, New York, 1971). These are monoazo, diarylide, condensation azo, isoindolinone, anthraquinone, and metal chelate pigments. Each group suffers from one or more disadvantages. Monoazo yellows generally have poor bleedfastness and marginal durability. Diarylide yellows have poor durability. Condensation azo yellows have marginal durability and are expensive to use. Isoindolinone and anthraquinone yellows have relatively low color strength and are expensive to use. Metal chelate yellows are dull, often green pigments which do not completely avoid the heavy metal problem.

The present invention relates to a new class of yellow to orange organic pigments. These new compounds provide bright intense colors which exhibit excellent bleedfastness and durability. They are particularly useful in the pigmentation of paints, plastics, and inks and they offer excellent alternatives to the potentially toxic inorganic pigments currently in use.

SUMMARY OF THE INVENTION

This invention relates to pigments which are derivatives of 5,6-benzocoumarin and 7,8-benzocoumarin and which have the formula:

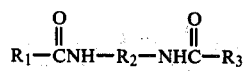

I where $R_1$ and $R_3$ are

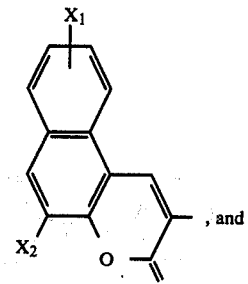

, and    II

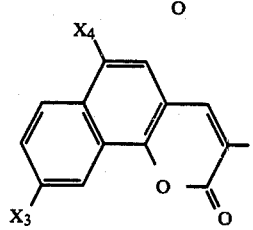

,    III and $R_2$ is

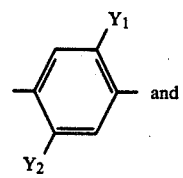

and    IV

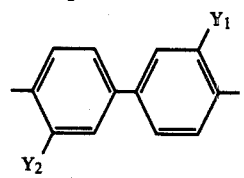

V wherein $X_1$ is hydrogen, alkyl of 1 to 4 carbon atoms, alkoxy of 1 to 4 carbon atoms, chlorine and bromine;

$X_2$ is hydrogen and CONHAr, wherein Ar is phenyl, and phenyl substituted with alkyl of 1 to 4 carbon atoms, alkoxy of 1 to 4 carbon atoms, chlorine, bromine, carbonamido, sulphonamido, benzimidazolone and phthalimido;

$X_3$ is hydrogen, alkyl of 1 to 4 carbon atoms, alkoxy of 1 to 4 carbon atoms, chlorine and bromine;

$X_4$ is hydrogen, alkyl of 1 to 4 carbon atoms, chlorine and bromine; and $Y_1$ and $Y_2$ may be the same or different and are each hydrogen, alkyl of 1 to 4 carbon atoms, alkoxy of 1 to 4 carbon atoms, chlorine and bromine.

DETAILED DESCRIPTION OF THE INVENTION

As stated above the present invention relates to a new class of organic pigments which vary in color from yellow to orange. These new compounds provide bright, intense colors which exhibit excellent bleedfastness and durability and are characterized by Formula I. The compounds of this invention are derived from benzocoumarins.

It will be understood that this invention includes pigments derived from benzocoumarin which are represented by the formulas:

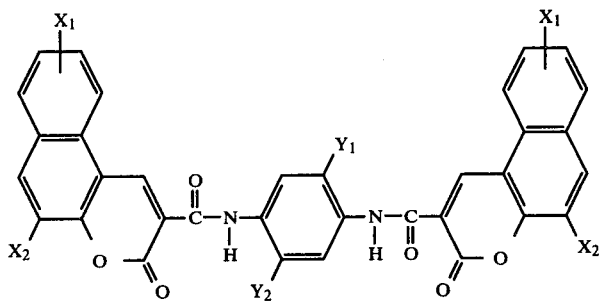

VI wherein
X₁ is hydrogen, alkyl of 1 to 4 carbon atoms, alkoxy of 1 to 4 carbon atoms, chlorine and bromine;

X₂ is hydrogen and CONHAr, wherein Ar is phenyl, and phenyl substituted with alkyl of 1 to 4 carbon atoms, alkoxy of 1 to 4 carbon atoms, chlorine, bromine, carbonamido, sulphonamido, benzimidazolone and phthalimide; and Y₁ and Y₂ are each hydrogen, alkyl of 1 to 4 carbon atoms, alkoxy of 1 to 4 carbon atoms, chlorine and bromine.

Y₁ and Y₂ are each hydrogen, alkyl of 1 to 4 carbon atoms, alkoxy of 1 to 4 carbon atoms, chlorine and bromine.

This invention further includes pigments derived from benzocoumarins which are represented by the following formulas:

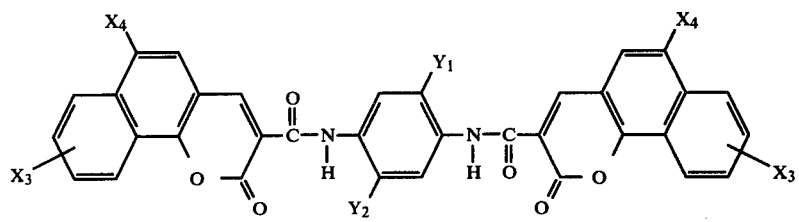

VIII wherein
X₃ is hydrogen, alkyl of 1 to 4 carbon atoms, alkoxy of 1 to 4 carbon atoms, chlorine and bromine;
X₄ is hydrogen, alkyl of 1 to 4 carbon atoms, chlorine and bromine; and

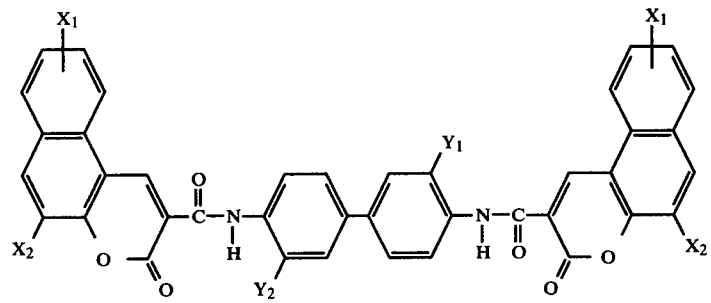

VII wherein
X₁ is hydrogen, alkyl of 1 to 4 carbon atoms, alkoxy of 1 to 4 carbon atoms, chlorine and bromine;

X₂ is hydrogen and CONHAr, wherein Ar is phenyl, and phenyl substituted with alkyl of 1 to 4 carbon atoms, alkoxy of 1 to 4 carbon atoms, chlorine, bromine, carbonamido, sulphonamido, benzimidazolone and phthalimido; and Y₁ and Y₂ are each hydrogen, alkyl of 1 to 4 carbon atoms, alkoxy of 1 to 4 carbon atoms, chloro and bromo.

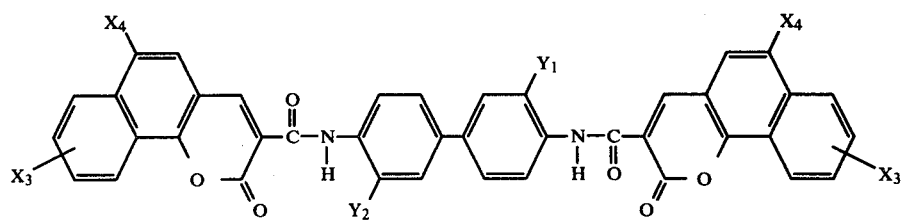

IX wherein
X₃ is hydrogen, alkyl of 1 to 4 carbon atoms, alkoxy of 1 to 4 carbon atoms, chlorine and bromine;
X₄ is hydrogen, alkyl of 1 to 4 carbon atoms, chlorine and bromine; and $Y_1$ and $Y_2$ are each hydrogen, alkyl of 1 to 4 carbon atoms, alkoxy of 1 to 4 carbon atoms, chlorine and bromine.

It will be understood that those compounds of Formulas VI to IX are preferred in which $X_1$, $X_3$, $X_4$, $Y_1$ and $Y_2$ are hydrogen, methyl and methoxy, and in which $X_2$ is hydrogen and CONHAr wherein Ar is phenyl substituted with methyl and methoxy.

The compounds of this invention can be prepared by various methods. The preferred method for preparing the compounds of this invention involves heating an appropriate benzocoumarin carbonyl chloride with an appropriate aromatic diamine in the presence of a suitable solvent such as o-dichlorobenzene, a mixture of toluene and triethylamine or Dowtherm ® A, a eutectic mixture consisting of 23.5 weight percent of biphenyl and 76.5 weight percent of diphenyl oxide.

An alternative method for preparing the compounds of this invention involves heating a carboxylic acid ester of an appropriate benzocoumarin with an appropriate aromatic diamine in the presence of an inorganic base and suitable solvent.

EXAMPLE 1

A mixture of 50 g of 5,6-benzocoumarin-3-carbonyl chloride, 10.5 g of p-phenylenediamine, and 1000 ml of o-dichlorobenzene is heated at 140°–150° C. for six hours. The product is isolated by filtration of the hot mixture, is washed with dimethylformamide, and is then washed with methanol. After drying, the yield is 50 g of N,N'-p-phenylene bis(3-oxo-3H-naphtho[2,1-b]pyran-2-carboxamide) as a yellow crystalline solid.

Anal. calculated for $C_{34}H_{20}N_2O_6$; C, 73.6; H, 3.9; N, 5.3; Found: C, 73.9; H, 3.7; N, 5.1.

EXAMPLE 2

A mixture of 13.4 g of ethyl-5,6-benzocoumarin-3-carboxylate, 2.7 g of p-phenylenediamine, 4.9 g of potassium acetate and 150 ml of Dowtherm ® A (an eutectic mixture of 23.5% of diphenyl and 76.5% of diphenyl oxide) is heated at 200° C. for 10 hours. The product is isolated by filtration of the reaction mixture and washed first with methanol, then water, then hot dimethylformamide. The yield is 9.2 g of N,N'-p-phenylene bis(3-oxo-3H-naphtho[2,1-b]pyran-2-carboxamide). Infrared and elemental analyses confirm that this product is identical to that prepared in Example 1.

EXAMPLE 3

A mixture of 3.0 g of 5,6-benzocoumarin-3-carbonyl chloride, 1.4 g of 2-chloro-p-phenylenediamine sulfate, 10 ml of triethylamine, and 100 ml of toluene is stirred at room temperature for one hour and then heated at 110° C. for four hours. The product is isolated by filtration of the hot mixture and washed first with methanol, then water, and then dimethylformamide. The compound is purified by extraction with 150 ml of boiling dimethylformamide. After drying, the yield is 1.1 g of N,N'-(2-chloro-1,4-phenylene)bis(3-oxo-3H-naphtho[2,1-b]pyran-2-carboxamide) as a reddish-yellow crystalline solid.

Anal. calculated for $C_{34}H_{19}N_2O_6Cl$; C, 69.6; H, 3.3; N, 4.8; Cl, 6.0; Found: C, 69.4; H, 3.7; N, 5.0, Cl, 7.1.

EXAMPLE 4

A mixture of 16.5 g of 2-methoxy-4-nitroaniline, 1.0 g of platinum oxide, and 200 ml of o-dichlorobenzene is shaken in a hydrogenation bomb in the presence of a constant 100 psi hydrogen atmosphere until hydrogen uptake ceases. The hydrogenation mixture is then heated to approximately 100° C. and filtered to remove platinum which is the hydrogenation catalyst. The filtrate is combined with 50 g of 5,6-benzocoumarin-3-carbonyl chloride and 300 ml of additional o-dichlorobenzene and heated at 150° C. for six hours. The product is collected by filtration. It is purified by mixing with 1000 ml of dimethylformamide, filtering, washing with methanol, and drying. The yield is 42.3 g of N,N'-(2-methoxy-1,4-phenylene)bis(3-oxo-3H-naphtho[2,1-b]pyran-2-carboxamide) as a reddish-yellow solid.

Anal. calculated for $C_{34}H_{20}N_2O_6$; C, 73.6; H, 3.9; N, 5.3; Found: C, 73.9; H, 3.7, N, 5.1.

EXAMPLE 5

A mixture of 17.5 g of 5,6-benzocoumarin-3-carbonyl chloride, 6.0 g of 2,5-dichloro-p-phenylene and 1000 ml of o-dichlorobenzene is heated at 150° C. for six hours. The compound is isolated by filtration and washed first with dimethylformamide and then methanol. After drying, the yield is 12.8 g of N,N'-(2,5-dichloro-1,4-phenylene)bis(3-oxo-3H-naphtho-[2,1-b]pyran-2-carboxamide) as a yellow crystalline solid.

Anal. calculated for $C_{35}H_{22}N_2O_7$; C, 65.7; H, 2.9; N, 4.5; O, 11.4; Found: C, 65.8; H, 3.3; N, 4.6; O, 11.4.

EXAMPLE 6

A mixture of 25 g of 5,6-benzocoumarin-3-carbonyl chloride, 8.1 g of 2,5-dimethoxy-p-phenylene-diamine and 1000 ml of o-dichlorobenzene is heated at 150° C. for six hours. The product is isolated by filtration and washed with dimethylformamide, then with methanol. After drying, the yield is 24 g of N,N'-(2,5-dimethoxy-1,4-phenylene)bis(3-oxo-3H-naphtho[2,1-b]pyran-2-carboxamide) as an orange crystalline solid.

Anal. calculated for $C_{36}H_{24}N_2O_8$; C, 70.6; H, 4.0; N, 4.6; Found: C, 70.8; H, 4.3; N, 4.5.

EXAMPLES 7-28

Additional compounds of this invention as listed in Table I can be prepared according to the procedure described in Example 1 by heating Reactant 1 and Reactant 2 to obtain the indicated product.

TABLE I

| Example No. | Reactant 1 | Reactant 2 | Product |
|---|---|---|---|
| 7 | naphtho-pyran-COCl | 2-methyl-1,4-phenylenediamine | N,N'-(2-methyl-1,4-phenylene)bis-(3-oxo-3H-naphtho-[2,1-b]pyran-2-carboxamide) |
| 8 | naphtho-pyran-COCl | 2,5-dimethyl-1,4-phenylenediamine | N,N'-(2,5-dimethyl-1,4-phenylene)-bis(3-oxo-3H-naphtho-[2,1-b]pyran-2-carboxamide) |
| 9 | naphtho-pyran-COCl | 2-methyl-5-chloro-1,4-phenylenediamine | N,N'-(2-methyl-5-chloro-1,4-phenylene)bis(3-oxo-3H-naphtho-[2,1-b]pyran-2-carboxamide) |
| 10 | naphtho-pyran-COCl | 2-chloro-5-methoxy-1,4-phenylenediamine | N,N'-(2-chloro-5-methoxy-1,4-phenylene)bis(3-oxo-3H-naphtho-[2,1-b]pyran-2-carboxamide) |
| 11 | naphtho-pyran-COCl | 4,4'-diaminobiphenyl | N,N'-4,4'-biphenylenebis(3-oxo-3H-naphtho-[2,1-b]pyran-2-carboxamide) |
| 12 | naphtho-pyran-COCl | 3,3'-dichloro-4,4'-diaminobiphenyl | N,N'-(3,3'-dichloro-4,4'-biphenylene)bis(3-oxo-3H-naphtho-[2,1-b]pyran-2-carboxamide) |

TABLE I-continued

| Example No. | Reactant 1 | Reactant 2 | Product |
|---|---|---|---|
| 13 | (2-hydroxy-naphthalene-1-yl)methylene malonyl chloride cyclic derivative | 3,3'-dimethylbenzidine (H2N-C6H3(CH3)-C6H3(CH3)-NH2) | N,N'-(3,3'-dimethyl-4,4'-biphenylene)bis(3-oxo-3H-naphtho-[2,1-b]pyran-2-carboxamide) |
| 14 | same naphthopyranone-COCl | 3,3'-dimethoxybenzidine (H2N-C6H3(OCH3)-C6H3(OCH3)-NH2) | N,N'-(3,3'-dimethoxy-4,4'-biphenylene)bis(3-oxo-3H-naphtho-[2,1-b]pyran-2-carboxamide) |
| 15 | 5-phenylcarbamoyl naphthopyranone-COCl (C6H5NH-CO- substituted) | p-phenylenediamine (H2N-C6H4-NH2) | N,N'-p-phenylenebis(3-oxo-5-phenylcarbamoyl-3H-naphtho-[2,1-b]pyran-2-carboxamide) |
| 16 | same as 15 | 2-chloro-1,4-phenylenediamine | N,N'-(2-chloro-1,4-phenylene)-bis(3-oxo-5-phenyl-carbamoyl-3H-naphtho[2,1-b]-pyran-2-carboxamide) |
| 17 | same as 15 | 2-methyl-1,4-phenylenediamine | N,N'-(2-methyl-1,4-phenylene)-bis(3-oxo-5-phenyl-carbamoyl-3H-naphtho[2,1-b]-pyran-2-carboxamide) |
| 18 | same as 15 | 2-methoxy-1,4-phenylenediamine | N,N'-(2-methoxy-1,4-phenylene)-bis(3-oxo-5-phenyl-carbamoyl-3H-naphtho[2,1-b]-pyran-2-carboxamide) |

TABLE I-continued

| Example No. | Reactant 1 | Reactant 2 | Product |
|---|---|---|---|
| 19 | (naphthalene with C₆H₅NH–C(=O)– substituent, –O–, and –CH=C(COCl)–C(=O)–) | 2,5-dimethoxy-1,4-phenylenediamine (H₂N–C₆H₂(OCH₃)₂–NH₂) | N,N'-(2,5-dimethoxy-1,4-phenylene)-bis(3-oxo-5-phenylcarbamoyl-3H-naphtho[2,1-b]-pyran-2-carboxamide) |
| 20 | 7-methylnaphthalene with –CH=C(COCl)–C(=O)–O– | p-phenylenediamine (H₂N–C₆H₄–NH₂) | N,N'-p-phenylenebis(3-oxo-8-methyl-3H-naphtho-[2,1-b]pyran-2-carboxamide) |
| 21 | 7-methylnaphthalene with –CH=C(COCl)–C(=O)–O– | 2-methoxy-1,4-phenylenediamine | N,N'-(2-methoxy-1,4-phenylene)-bis(3-oxo-8-methyl-3H-naphtho-[2,1-b]pyran-2-carboxamide) |
| 22 | 7-methylnaphthalene with –CH=C(COCl)–C(=O)–O– | 2-chloro-1,4-phenylenediamine | N,N'-(2-chloro-1,4-phenylene)-bis(3-oxo-8-methyl-3H-naphtho-[2,1-b]pyran-2-carboxamide) |
| 23 | 6-methylnaphthalene with –CH=C(COCl)–C(=O)–O– | p-phenylenediamine (H₂N–C₆H₄–NH₂) | N,N'-p-phenylenebis(3-oxo-9-methyl-3H-naphtho-[2,1-b]pyran-2-carboxamide) |

TABLE I-continued

| Example No. | Reactant 1 | Reactant 2 | Product |
|---|---|---|---|
| 24 | 7-methyl-naphtho[2,1-b]pyran-3-oxo-2-carbonyl chloride | 2-methoxy-1,4-phenylenediamine | N,N'-(2-methoxy-1,4-phenylene)-bis(3-oxo-9-methyl-3H-naphtho-[2,1-b]pyran-2-carboxamide) |
| 25 | 7-methyl-naphtho[2,1-b]pyran-3-oxo-2-carbonyl chloride | 2-chloro-1,4-phenylenediamine | N,N'-(2-chloro-1,4-phenylene)-bis(3-oxo-9-methyl-3H-naphtho-[2,1-b]pyran-2-carboxamide) |
| 26 | 6-chloro-naphtho[2,1-b]pyran-3-oxo-2-carbonyl chloride | p-phenylenediamine | N,N'-p-phenylenebis(3-oxo-8-chloro-3H-naphtho-[2,1-b]pyran-2-carboxamide) |
| 27 | 6-chloro-naphtho[2,1-b]pyran-3-oxo-2-carbonyl chloride | 2-methoxy-1,4-phenylenediamine | N,N'-(2-methoxy-1,4-phenylene)-bis(3-oxo-8-chloro-3H-naphthol-[2,1-b]pyran-2-carboxamide) |
| 28 | 6-chloro-naphtho[2,1-b]pyran-3-oxo-2-carbonyl chloride | 2-chloro-1,4-phenylenediamine | N,N'-(2-chloro-1,4-phenylene)-bis(3-oxo-8-chloro-3H-naphtho-[2,1-b]pyran-2-carboxamide) |

EXAMPLE 29

A mixture of 15 g of 7,8-benzo-6-chlorocoumarin-3-carbonyl chloride, 2.76 g of p-phenylenediamine and 300 ml of o-dichlorobenzene is heated at 140° C. for five hours. The product precipitates and is collected by filtration of the hot reaction mixture. The product is washed thoroughly with methanol and dried to give 15.4 g (95% of theoretical) of N,N'-p-phenylene(2-oxo-2H-6-chloro-naphtho[1,2-b]pyran-3-carboxamide) as a bright yellow material.

Anal. calculated for $C_{34}H_{18}N_2O_6Cl_2$: C, 65.71; H, 2.92; N, 4.51; Cl, 11.41. Found: C, 65.78; H, 3.15; N, 4.49; Cl, 12.00.

EXAMPLE 30

A mixture of 14 g of 7,8-benzo-6-chlorocoumarin-3-carbonyl chloride, 3.37 g of 2-methoxy-p-phenylenediamine (prepared by the hydrogenation of 4.1 g of 2-methoxy-4-nitroaniline), and 300 ml of o-dichlorobenzene is heated at 150° C. for five hours. The product precipitates and is collected by filtration of the hot reaction mixture. The product is washed thoroughly with methanol and dried to give 10.6 g (68% of theoretical) of N,N'-(2'-methoxy-1,4-phenylene)bis(2-oxo-2H-6-chloro-naphtho[1,2-b]pyran-3-carboxamide) as a bright orange material.

Anal. calculated for $C_{35}H_{20}N_2O_7Cl_2$: C, 64.53; H, 3.09; N, 4.30; Cl, 10.89. Found: C, 64.37; H, 3.32; N, 4.11; Cl, 11.20.

EXAMPLES 31–42

Additional compounds of this invention as listed in Table II can be prepared according to the procedure described in Example 29 by heating Reactant 1 and Reactant 2 as taught in Example 29 to obtain the indicated product.

TABLE II

| Example No. | Reactant 1 | Reactant 2 | Product |
|---|---|---|---|
| 31 | (4-chloro-naphtho-coumarin-3-carbonyl chloride) | 2-chloro-1,4-phenylenediamine | N,N'-(2-chloro-1,4-phenylene)bis-(2-oxo-6-chloro-2H-naphtho-[1,2-b]pyran-3-carboxamide) |
| 32 | (4-chloro-naphtho-coumarin-3-carbonyl chloride) | 2-methyl-1,4-phenylenediamine | N,N'-(2-methyl-1,4-phenylene)bis-(2-oxo-6-chloro-2H-naphtho-[1,2-b]pyran-3-carboxamide) |
| 33 | (4-chloro-naphtho-coumarin-3-carbonyl chloride) | 2-chloro-5-methyl-1,4-phenylenediamine | N,N'-(2-chloro-5-methyl-1,4-phenylene)bis-(2-oxo-6-chloro-2H-naphtho[1,2-b]pyran-3-carboxamide) |
| 34 | (4-chloro-naphtho-coumarin-3-carbonyl chloride) | 2,5-dichloro-1,4-phenylenediamine | N,N'-(2,5-dichloro-1,4-phenylene)bis-(2-oxo-6-chloro-2H-naphtho[1,2-b]pyran-3-carboxamide) |
| 35 | (4-chloro-naphtho-coumarin-3-carbonyl chloride) | 2,5-dimethoxy-1,4-phenylenediamine | N,N'-(2,5-dimethoxy-1,4-phenylene)-bis(2-oxo-6-chloro-2H-naphtho-[1,2-b]pyran-3-carboxamide) |
| 36 | (4-chloro-naphtho-coumarin-3-carbonyl chloride) | 2-chloro-5-methoxy-1,4-phenylenediamine | N,N'-(2-chloro-5-methoxy-1,4-phenylene)bis(2-oxo-6-chloro-2H-naphtho[1,2-b]pyran-3-carboxamide) |

TABLE II-continued

| Example No. | Reactant 1 | Reactant 2 | Product |
|---|---|---|---|
| 37 | (4-chloro naphthopyranone acid chloride) | $H_2N$—biphenyl—$NH_2$ | N,N'-4,4'-biphenylenebis(2-oxo-6-chloro-2H-naphtho[1,2-b]pyran-3-carboxamide) |
| 38 | (4-chloro naphthopyranone acid chloride) | 3,3'-dichlorobenzidine | N,N'-(3,3'-dichloro-4,4'-biphenylene)-bis(2-oxo-6-chloro-2H-naphtho[1,2-b]-pyran-3-carboxamide) |
| 39 | (4-chloro naphthopyranone acid chloride) | 3,3'-dimethoxybenzidine | N,N'-(3,3'-dimethoxy-4,4'-biphenylene)-bis(2-oxo-6-chloro-2H-naphtho[1,2-b]-pyran-3-carboxamide) |
| 40 | (4-methyl naphthopyranone acid chloride) | p-phenylenediamine | N,N'-p-phenylenebis(2-oxo-6-methyl-2H-naphtho[1,2-b]pyran-3-carboxamide) |
| 41 | (4-methyl naphthopyranone acid chloride) | 2-chloro-1,4-phenylenediamine | N,N'-(2-chloro-1,4-phenylene)bis-(2-oxo-6-methyl-2H-naphtho-[1,2-b]pyran-3-carboxamide) |
| 42 | (4-methyl naphthopyranone acid chloride) | 2-methoxy-1,4-phenylenediamine | N,N'-(2-methoxy-1,4-phenylene)bis-(2-oxo-6-methyl-2H-naphtho[1,2-b]pyran-3-carboxamide) |

What is claimed is:

1. A compound of the formula

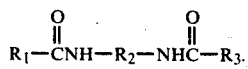

where $R_1$ and $R_3$ are

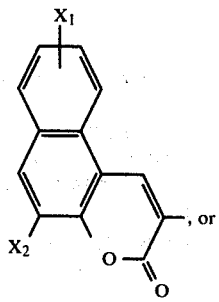

, or

-continued

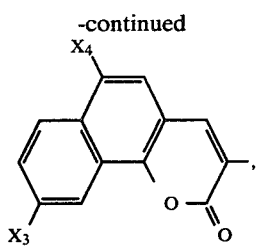

and R₂ is

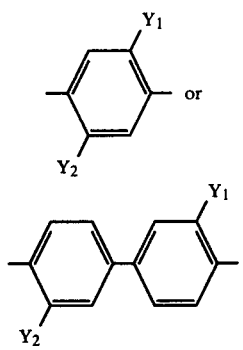

wherein
$X_1$ is hydrogen, alkyl of 1 to 4 carbon atoms, alkoxy of 1 to 4 carbon atoms, chlorine or bromine;
$X_2$ is hydrogen or CONHAr, wherein Ar is phenyl and phenyl substituted with alkyl of 1 to 3 carbon atoms, alkoxy of 1 to 4 carbon atoms, chlorine, bromine, carbonamido, sulphonamido, or phthalimido;
$X_3$ is hydrogen, alkyl of 1 to 4 carbon atoms, alkoxy of 1 to 4 carbon atoms, chlorine or bromine;
$X_4$ is hydrogen, alkyl of 1 to 4 carbon atoms, chlorine or bromine; and
$Y_1$ and $Y_2$ are each hydrogen, alkyl of 1 to 4 carbon atoms, alkoxy of 1 to 4 carbon atoms, chlorine or bromine.

2. A compound of the formula

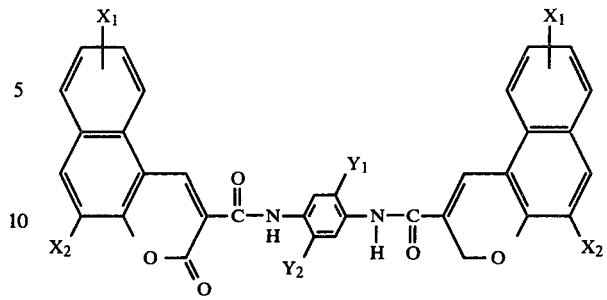

wherein
$X_1$ is hydrogen, alkyl of 1 to 4 carbon atoms, alkoxy of 1 to 4 carbon atoms, chlorine or bromine;
$X_2$ is hydrogen and CONHAr, wherein Ar is phenyl and phenyl substituted with alkyl of 1 to 3 carbon atoms, alkoxy of 1 to 4 carbon atoms, chlorine, bromine, carbonamido, sulphonamido, or phthalimide; and
$Y_1$ and $Y_2$ are each hydrogen, alkyl of 1 to 4 carbon atoms, alkoxy of 1 to 4 carbon atoms, chlorine or bromine.

3. A compound of claim 2 where $X_1$ is hydrogen, methyl, methoxy, chlorine or bromine; $X_2$ is hydrogen or CONHAr, where Ar is phenyl and phenyl substituted with alkyl of 1 to 3 carbon atoms, alkoxy of 1 to 4 carbon atoms, chlorine, bromine, carbonamido, sulphonamido, or phthalimide; and $Y_1$ and $Y_2$ are each hydrogen, methyl, methoxy, chlorine or bromine.

4. A compound of the formula

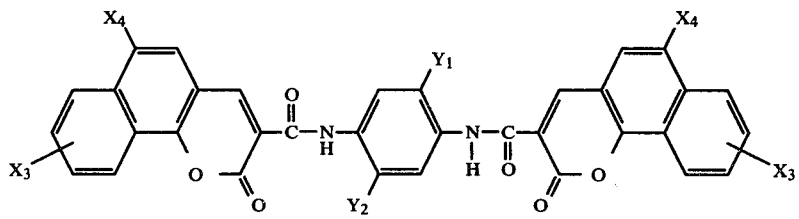

wherein
$X_3$ is hydrogen, alkyl of 1 to 4 carbon atoms, alkoxy of 1 to 4 carbon atoms, chlorine or bromine;
$X_4$ is hydrogen, alkyl of 1 to 4 carbon atoms, chlorine or bromine; and
$Y_1$ and $Y_2$ are each hydrogen, alkyl of 1 to 4 carbon atoms, alkoxy of 1 to 4 carbon atoms, chlorine or bromine.

5. A compound of claim 4 wherein $X_3$ is hydrogen, methyl, chlorine or bromine; $X_4$ is hydrogen, methyl, methoxy, chlorine or bromine; and $Y_1$ and $Y_2$ are each hydrogen, methyl, methoxy, chlorine or bromine.

6. A compound of the formula

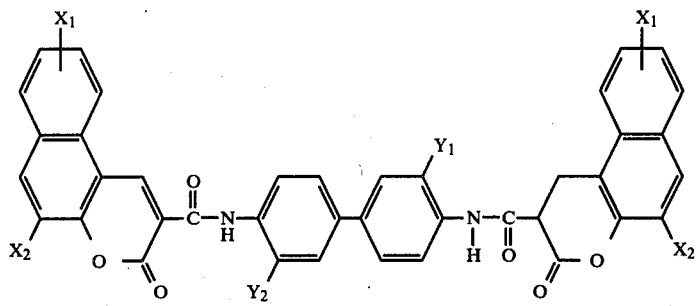

wherein
X$_1$ is hydrogen, alkyl of 1 to 4 carbon atoms, alkoxy of 1 to 4 carbon atoms, chlorine or bromine;

X$_2$ is hydrogen or CONHAr, wherein Ar is phenyl and phenyl substituted with alkyl of 1 to 3 carbon atoms, alkoxy of 1 to 4 carbon atoms, chlorine, bromine, carbonamide, sulphonamido, or phthalimido; and Y$_1$ and Y$_2$ are each hydrogen, alkyl of 1 to 4 carbon atoms, alkoxy of 1 to 4 carbon atoms, chlorine or bromine.

7. A compound of claim 6 wherein X$_1$ is hydrogen, methyl, methoxy, chlorine or bromine; X$_3$ is hydrogen or CONHAr, wherein Ar is as defined in claim 10; and Y$_3$ and Y$_4$ are each hydrogen, methyl, methoxy, chlorine or bromine.

8. A compound of the formula

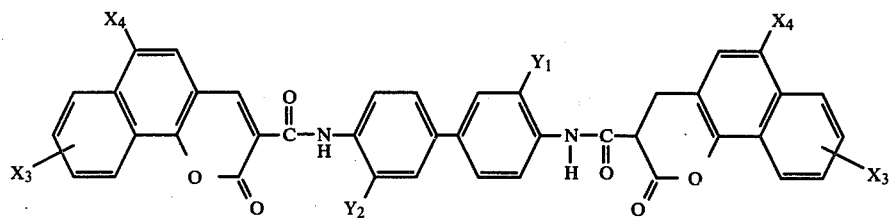

wherein
X$_3$ is hydrogen, alkyl of 1 to 4 carbon atoms, alkoxy of 1 to 4 carbon atoms, chlorine or bromine;
X$_4$ is hydrogen, alkyl of 1 to 4 carbon atoms, chlorine or bromine; and
Y$_1$ and Y$_2$ are each hydrogen, alkyl of 1 to 4 carbon atoms, alkoxy of 1 to 4 carbon atoms, chlorine or bromine.

9. A compound of claim 8 where X$_3$ is hydrogen, methyl, methoxy, chlorine or bromine; X$_4$ is hydrogen, methyl, chlorine or bromine; and Y$_1$ and Y$_2$ are each hydrogen, methyl, methoxy, chlorine or bromine.

* * * * *

UNITED STATES PATENT OFFICE
CERTIFICATE OF CORRECTION

PATENT NO. : 4,177,195
DATED : December 4, 1979
INVENTOR(S) : Richard C. Bingham It is certified that error appears in the above-identified patent and that said Letters Patent are hereby corrected as shown below:

In the Claims the structural formula appearing at column 20, lines 1-10 should appear as follows:

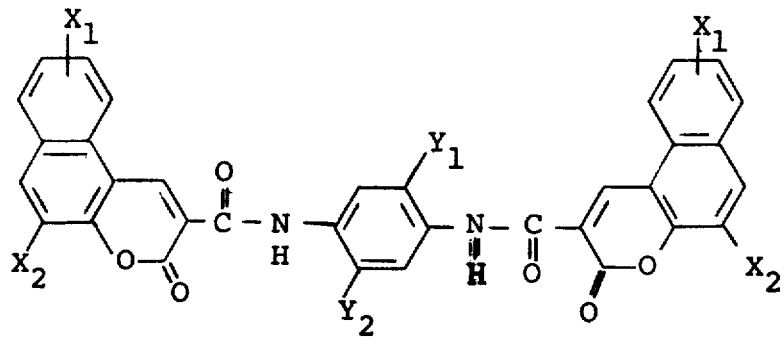

In Claim 7, column 21, line 40, that portion of the claim reading "wherein Ar is as defined in claim 10" should read --wherein Ar is as defined in claim 1--.

Signed and Sealed this

Twentieth Day of May 1980

[SEAL]

Attest:

SIDNEY A. DIAMOND

Attesting Officer

Commissioner of Patents and Trademarks